United States Patent [19] [11] 4,056,445
Gauntt et al. [45] Nov. 1, 1977

[54] DETERMINATION OF CORROSION RATES BY AN ELECTROCHEMICAL METHOD

[76] Inventors: Wayne M. Gauntt, 1825 Wheaton Ave., Claremont, Calif. 91711; Earl L. Pye, 2910 Santez Drive, Pomona, Calif. 91768

[21] Appl. No.: 744,972

[22] Filed: Nov. 26, 1976

Related U.S. Application Data

[63] Continuation-in-part of Ser. No. 621,550, Oct. 10, 1975, abandoned, and a continuation-in-part of Ser. No. 538,763, Jan. 6, 1975, abandoned.

[51] Int. Cl.$^2$ ..................... G01N 27/46; G01N 27/30
[52] U.S. Cl. ................................. 204/1 T; 204/195 C
[58] Field of Search ........................... 204/1 C, 195 C

[56] References Cited

U.S. PATENT DOCUMENTS 3,855,101  12/1974  Wilson ............................ 204/195 R

OTHER PUBLICATIONS

H. Ailor, Editor, "Handbook on Corrosion Testing & Evaluation," Wiley, N. Y. (1971), pp. 182-183.
S. Barnartt, "Two-Point & Three-Point Methods for the Investigation of Electrode Reaction Mechanisms," Electrochimica Acta, vol. 15, pp. 1313-1324, (1970).

Primary Examiner—John H. Mack
Assistant Examiner—Aaron Weisstuch
Attorney, Agent, or Firm—Boniard I. Brown

[57] ABSTRACT

A method for the rapid determination of corrosion rates on a metallic material immersed in an electrolyte employs an electrochemical cell including at least one electrode of the material whose corrosion rate is to be determined and at least one other electrode also immersed in the same electrolyte. External forcing and measuring circuits are provided by means of which a first potential may be impressed across the immersed electrodes and the resulting current flow measured; the same circuits are also employed to impress a second potential and to measure the resulting current. Both said first and second potentials are so selected that they lie within the characteristic of the corroding cell governed by the exponential Tafel relationship. The freely corroding current for the test electrode is then determined by extrapolating the Tafel curve to zero impressed potential. The freely corroding current is then manipulated graphically or mathematically to give the corrosion rate in appropriate units.

20 Claims, 7 Drawing Figures

ADC = ANALOG TO DIGITAL CONVERTER
DAC = DIGITAL TO ANALOG CONVERTER
C = COUNTER ELECTRODE
R = REFERENCE ELECTRODE
W = WORKING ELECTRODE

DETERMINATION OF CORROSION RATES BY AN ELECTROCHEMICAL METHOD

RELATED APPLICATIONS

This application is a continuation-in-part of application Ser. No. 621,550, filed Oct. 10, 1975, now abandoned, which, in turn, is a continuation-in-part of application Ser. No. 538,763, filed Jan. 6, 1975, now abandoned.

BACKGROUND OF THE INVENTION

1. Field of the Invention

This invention relates to an improved method for the determination of the corrosion rate of a metallic substance immersed in an electrolyte. It relates, more particularly, to a method employing the principles of electrochemistry and permits rapid, essentially instantaneous, measurements of the long-term corrosion rate.

The rate at which a metallic material is degraded at the surface in contact with a corrosive medium — a chemically active fluid, moist earth, salt spray, or other — is of considerable interest to the designers of metal structures and to those who provide protective coatings, inhibitors and other materials designed to slow down the rate of metal loss.

2. Discussion of the Prior Art

The traditional method most widely employed in the art of corrosion rate measurement is the exposure of a test coupon to the corrosive medium and the periodic removal of the coupon to determine the corrosion rate by weighing the remaining, unaffected metal. A variant on the above method employs an elongated test coupon of known initial electrical resistance and the periodic measurement of that quantity to determine the change in cross-sectional area and, hence, the weight loss.

These methods have inherent disadvantages: foremost the length of time required to obtain meaningful loss of material. Most corrosion rates are expressed in units of mils per year; that is, a surface exposed to the test conditions will lose so many thousandths of an inch per year through chemical attack. Because of the slowness of the reactions involved it takes months, and sometimes years, of exposure to obtain valid results and the experimental parameters must be closely controlled throughout such lengthy periods, often at great expense.

Another method of the art has been developed more recently and is based on fundamental concepts of corrosion as a result of electrochemical action. The basic expression of such concepts relies on Faraday's Law which, in a readily employed form, states that the weight of metal dissolved (W) is a function of the corroding current ($I_{corr}$), the time of exposure to the current flow ($t$) and a fundamental property of the metal subjected to the corrosive environment ($e$). A constant (F) converts the above relationship to an equality, the value of F being well-known and corresponding to 96,500 coulombs of electrical charge. The equation is simply stated as:

$$W = 1/F \times I_{corr} \times t \times e$$

While Faraday's Law is universally accepted as valid and three of the four parameters on the right side are known, or readily defined, the application of the low to the determination of corrosion rates requires a knowledge of the corrosion current ($I_{corr}$) under the applicable circumstances.

Because the corrosion current is a specific result of the particular corrosion cell which is created by the placement of a particular metallic body into the particular electrolyte under the particular environmental conditions for which the corrosion rate is sought, and because any attempt to measure it would alter the circumstances of the corrosion process, direct measurement of $I_{corr}$ is extremely difficult and would require elaborate procedures.

It is, however, possible to alter the circumstances of the corrosion process deliberately and to relate experimental measurements of currents so obtained back to an approximate value of the true $I_{corr}$.

This method of the prior art is known as the Linear Polarization or Polarization Resistance method and is generally based on the Stern-Geary equation, as reported in the Journal of the Electrochemical Society, 104, 56 of 1957.

In the application of the polarization resistance method to the measurement of corrosion rates advantage is taken of the near linear relationship between a small impressed potential and the resulting increment in corrosion current. The metallic material whose behavior is to be studied is made part of a multi-electrode electrolytic cell whose electrolyte is identical to that in the proposed application. An external potential source is connected across the cell and the current flowing in the circuit, through the electrolyte and the electrode representing the metal under study, is measured. A new variable, the Polarization Resistance ($R_p$) is then defined as the ratio of the small impressed potential ($\Delta E_{app}$) to the resulting current ($\Delta I_{app}$), with the value of the applied potential generally held at, or near, a value of 10 millivolts. Therefore:

$$R_p = (\Delta E_{app}/\Delta I_{app}), \Delta E_{app} \rightarrow 0$$

When the above information is known, then the value of $I_{corr}$ can be derived from the relationship $$I_{corr} = K/R_p$$

where the factor K is a function of the Tafel exponents defining the current flow under the circumstances where the well-known Tafel relationship applies. The Tafel Law states that the current flowing in such a circuit ought to be an exponential function of the applied voltage and it generally holds at high impressed potentials, above approximately 50 millivolts. These exponents are defined in terms of the potential increment required to effect a tenfold increase in the current flow and are different in value for the cases where the corrosion specimen is made the anode, or cathode, of the corrosion cell, respectively, by reversing the polarity of the impressed voltage.

The value of K relates to the anodic and cathodic Tafel exponents — generally known as Tafel slopes in the are — by the equality:

$$K = \frac{B_a \times B_c}{2.303(B_a + B_c)}$$

where $B_a$ and $B_c$ are the anodic and cathodic exponents, respectively, and 2.303 is a constant interrelating the value of natural logarithms and logarithms to the base 10; its presence is predicated on the aforementioned definitions of $B_a$ and $B_c$ in representing a tenfold increase in current.

In the techniques of the prior art, experimental determination is restricted to the value of $R_p$ and K is expressed in terms of assumed values of $B_a$ and $B_c$, conventionally at 120 millivolts per decade. The advantage attendant on this procedure is the quickness with which experimental results are obtained, in a few minutes as opposed to months with the coupon immersion techniques; special corrosion cells and instrumentation have been developed to make the measurements simple and, in the terms of the art, substantially 'instantaneous'.

Nevertheless, the assumptions regarding the values of the Tafel slopes introduce errors which can be, and often are, of considerable influence.

It is, therefore, a primary object of the invention to teach a novel method of corrosion rate determination which encompasses the experimental measurement of the potential/current relationship in the region obeying the exponential Tafel relationship and, thereby, increases the accuracy and reliability of substantially instantaneous corrosion rate measurements.

It is a further object of the invention to teach the use of such a method in corrosion cells incorporating a plurality of conducting electrodes, two to five in number.

It is yet another object of the invention to teach the construction and use of manual and automated apparatus for the performance of the method described above.

SUMMARY OF THE INVENTION

The novel method of the invention utilizes corrosion cells wherein a plurality of conducting electrodes are immersed in an electrolytic bath whose composition, temperature and concentration correspond to that for which the corrosion rate is to be determined. At least one of the aforementioned electrodes is composed of the metal, alloy or composition whose corrosion rate is to be determined, and is referred to as the "working" electrode. Another electrode is provided as the reference point for the potential measurements of the experiment and is known as the "reference" electrode, while a third electrode acts as a part of the path for the externally induced current flow, and is known as the "counter" electrode.

In some variants of the method the number of electrodes is varied by combining the functions of the reference and counter electrodes, or by providing more than one electrode for similar functions, but the above three-electrode configuration is employed by preference in the method of the invention.

Instrumentation is provided to measure the current flowing through the electrical path interconnecting the working and counter electrodes external to the electrolytic bath, and to measure the electrical potential between the reference and working electrodes.

A first potential is impressed across the forcing circuit of the apparatus — its value lying between 50 millivolts and 200 millivolts — and the resulting current determined, after the elapse of a specified time period — generally between 10 and 50 in duration.

A second potential, higher in magnitude than the aforementioned first potential — selected in the region between 100 and 400 millivolts and generally not higher than 800 or 1,000 millivolts — is then impressed on the circuit and a current measurement made, again after the passage of the previously chosen time period.

These potentials, and the currents resulting from their application, are then utilized to define a nonequilibrium Tafel slope for the corroding system, and for the selected polarity of the working electrode.

It is a distinct feature of the method of the invention that no attempt is made to attain equilibrium conditions, the time periods used are at least one order of magnitude lower than necessary to establish time-invariant reaction rates. The method of the invention relies on the insight that a transitory time period exists during which the current flowing in the corrosion cell is related to the current flowing in the same cell at equilibrium.

By plotting the exponential curve defined by the aforementioned pair of potential/current measurements — most conveniently represented by a straight line on semi-logarithmic graph paper — it is possible to extrapolate the 'nonequilibrium' Tafel function back to an imaginary point where the impressed potential is zero. The value of the current corresponding to zero impressed potential can be shown to be equivalent to the value of $I_{corr}$ in the Faraday relationship discussed above.

Since the method of the invention is only concerned with the determination of the freely corroding current rate, either of the anodic and cathodic branches of the Tafel region may be utilized; the intercept — the value of $I_{corr}$ — will be the same for the two, even where the slopes $B_a$ and $B_c$ differ in value.

It is, therefore, apparent that the instant method will provide an experimentally derived value of the freely corroding current of the metal/electrolyte combination rapidly, without the interposition of assumed factors to render the results so obtained questionable.

In a preferred form of the apparatus for the mechanization of the method described hereinabove, electronic circuitry is provided to rapidly subject a corrosion cell to the various potentials in succession and to record the appropriate current measurements upon the elapse of the prescribed time period. The results are held in an integral computing circuit which drives a numeric display directly offering the value of $I_{corr}$.

Other details, advantages and objects of the invention will become apparent from the detailed description thereof below, and from reference to the diagrams and graphs of the accompanying drawings.

DESCRIPTION OF THE PREFERRED EMBODIMENT

The method of the invention utilizes certain characteristics of a corrosion cell including a metal electrode of the material under test and the electrolyte to which it is to be exposed. When subjected to an externally imposed — or "applied" — potential, the current flowing between a counter electrode and the working electrode, sometimes called test electrode, is a function of the rate of material removal from, or deposition on, the working electrode. A typical set of curves showing the dependence of the current density on the applied potential is shown in FIG. 1.

Figure 1:
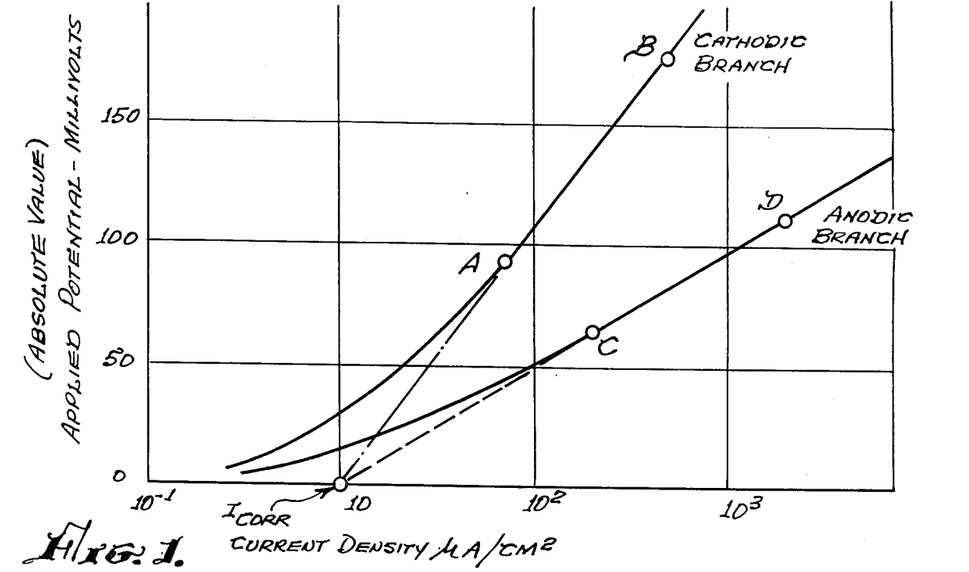
FIG. 1 is a graph indicating typical relationships for corrosion current as a function of the impressed voltage.

The abscissa of the diagram of FIG. 1 shows the current density plotted on logarithmic — or ratio scale — coordinates, while the absolute value of the applied potential is plotted on the ordinate in linear coordinates. The experimentally determined relationship between the applied potential and the induced current density shows a region, in which the Tafel Law applies, where that dependence is exponential, and the graph becomes a straight line in the semi-logarithmic coordinates of FIG. 1.

Two separate curves are shown, one for the anodic and the other for the cathodic polarity of the working electrode with respect to the counter electrode. While the two branches show similar tendencies, the exponent governing the current/potential dependency for the cathodic branch is different from that for the anodic branch, indicating one of the common sources of error involved in the Polarization Resistance methods, where the slopes of the straight line segments of the curves are assumed to be equal.

For the particular experimental conditions plotted as an example, the cathodic Tafel slope is approximately 120 millivolts/decade, while the anodic slope is of the order of 50 millivolts/decade.

Because they are straight lines in semi-logarithmic coordinates, the two branches of the polarization diagram — as the type of graph represented by FIG. 1 is generally called — can be defined, for the Tafel Law region, by a pair of measurements each, typically shown as points 'A' and 'B' for the cathodic branch and points 'C' and 'D' for the anodic branch, respectively.

It will be noted that both the anodic and cathodic branches may be extrapolated to an intercept representing zero applied voltage, the condition corresponding to free corrosion, and that the intercepts for the two branches converge to the same point. This intercept at zero impressed potential corresponds to no experimentally measurable condition in the corroding system, but it can be shown to be equivalent to the freely corroding current density $i_{corr}$. It is, therefore, evident that the method of the invention, based on the determination of the paired coordinates defining either branch of the Tafel region of the polarization diagram, may be utilized to determine the freely corroding current density, by determining the intercept of the resulting exponential curve.

It has been conventional in the art to take measurements of impressed — or forcing — potential and the resulting current under conditions of stable equilibrium. Such an approach has many practical disadvantages, notably in the time required to reach such an equilibrium state — conventionally at least 1 minute for each 10 millivolt increment in potential, as quoted, for example, in ASTM Procedure 05 — and in the even longer periods required to depolarize the electrodes. The method of the invention avoids such lengthy time increments by making the determination of current a specified period of time — much shorter than that required to attain equilibrium — after the potential is imposed. The resulting pairs of points define a new exponential function, a non-equilibrium equivalent to the true Tafel curve, which has been found by experiment to lead to the same intercept defining the freely corroding current rate as the method of the prior art.

Figure 2:
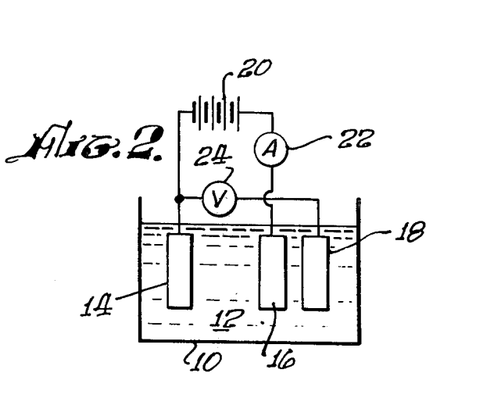
FIG. 2 is a schematic diagram indicating the test cell for making corrosion current determination with apparatus including three test electrodes.

By preference, the method of the invention utilizes an experimental set-up wherein, as shown in the diagram of FIG. 2, three conducting electrodes are immersed in the electrolyte whose action on the subject metal composition, represented in the 'working' electrode, is to be determined. An electrolytic bath 12 is contained in a vessel 10 — in the apparatus of FIG. 2 — and three electrodes — a working electrode 14, a counter electrode 16 and a reference electrode 18 — are immersed therein.

A source of direct current potential, typically a battery 20, is connected across the working electrode 14 and counter electrode 16. The applied potential is determined by a voltmeter 24 connected between the working and reference electrodes, and the induced current is measured by an ammeter 22 interposed between the battery 20 and the counter electrode 16 in the conducting path external to the electrolyte 12.

In a typical variant of the method of the invention the counter electrode 16 is made identical to the working electrode 14, while the material for the reference electrode 18 is selected from the group of materials generally utilized in the art as Standard Electrochemical Reference Electrodes. This group includes, amoung others, several metals, alloys, and electrochemical electrodes such as platinum, calomel electrode, copper/copper sulphate electrode, and silver/silver chloride electrode.

In performing the measurements of the method, a first applied voltage would be applied by battery 20 across the reference and counter electrodes such that the resulting potential, as measured by the voltmeter 24, between the working electrode and reference electrode would be a specific value selected from the range 50 to 200 millivolts, and the resulting current observed on ammeter 22. The applied potential and resulting current would then define a point, corresponding to point 'A' of FIG. 1, in the polarization graph for the corroding system.

A second potential, at a higher absolute value and selected from the range of 100 to 400 millivolts, would then be applied across the working and reference electrodes and the resulting current recorded. This measurement would then define another point on the polarization graph, corresponding to point 'B' of FIG. 1. The freely corroding current $I_{corr}$ would then be determined by either graphical methods, recording the above results on semi-logarithmic graph paper and extrapolating a straight line through them to the zero applied potential level, or by mathematical methods, substituting the experimental results in the equation:

$$\log(I_{corr}) = \log(I_A) + \left( \frac{1}{1 - \frac{e_B}{e_A}} \right) (\log(I_B) - \log(I_A))$$

where $I_A$, $I_B$, $e_A$, and $e_B$ are, respectively, the measured values of the current (or current density) and of the applied potential at the points 'A' and 'B'.

In another version of the method the second measurement may be made by reversing the polarity of the battery 20 and of the ammeter 22 and performing the test with electrode 16 as the working electrode and electrode 14 as the counter electrode.

It is also possible to perform the above test in a cell wherein all three electrodes are made from the material under test and in which the assignment of the reference electrode is arbitrary and is determined by the interconnection of the voltmeter 24 and the ammeter 22.

It is also possible to perform the above method in a cell wherein both the reference and counter electrodes are different from the working electrode 14 in material — and with the counter and reference electrodes either identical to each other or made from different materials — with the polarity of the battery being such that all readings taken on the working electrode are of the same polarity, the polarity being reversed between each pair of successive readings.

Figure 3:
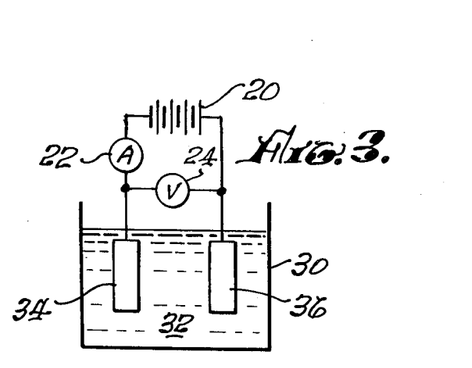
FIG. 3 is another schematic diagram showing test arrangements utilizing two electrodes.

A variant of the method of the invention employs a corrosion cell of the configuration schematically depicted in FIG. 3, including a container 30, a body of liquid electrolyte 32, a working electrode 34 and a counter electrode 36. No reference electrode is provided and its function is assumed by either electrode. The counter electrode 36 is made of a conducting material, suitably, but not necessarily, of the same material as the working electrode 34.

Electrical conductors interconnect the working and counter electrodes with an external forcing circuit including a battery 20, an ammeter 22 and a voltmeter 24. The voltmeter 24 is connected across the counter and working electrodes and measures the potential difference developed by the battery 20, while the ammeter 22 is used to determine the current flowing through the electrolytic bath 32 between the working and counter electrodes.

To measure the freely corroding current $I_{corr}$ in the system of FIG. 3 a first potential, larger than 50 millivolts but less than 200 millivolts in magnitude, is impressed across the external circuit by battery 20 and the resulting current determined by means of ammeter 22. A higher absolute potential, in the range between 100 and 400 millivolts, is then developed by the battery 20 — or by another battery of higher nominal voltage rating — and the resulting current measured. The two pairs of corresponding potential and current measurements are then plotted on semi-logarithmic paper and the intercept of the extrapolated straight line between these points obtained as the value of $I_{corr}$ or by the previously mentioned mathematical method.

It should be noted at this point that while the method generally refers to an applied voltage and a resulting current, the same result may be obtained by causing a desired value of current to flow in the circuit and measuring the potential required to induce that current. The two approaches are identical in result — as long as the resulting potential levels lie in the Tafel range of the polarization diagram, above the approximately 50 millivolt level — and affect only the nature and control of the external forcing circuit.

Figure 4:
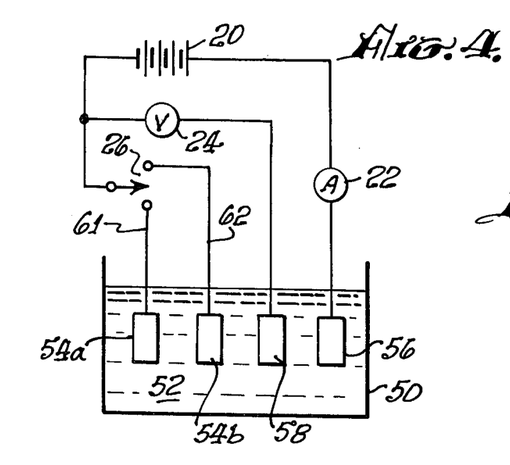
FIG. 4 is a schematic diagram with four test electrodes, including paired working electrodes, for the performance of the method of the invention.

The corrosion cell shown in FIG. 4 comprises four electrodes, of which at least two — a working electrode 54a and a second working electrode 54b — are made from the material under test. The outer electrodes are: a reference electrode 58 and a counter electrode 56. All four electrodes are immersed in an electrolyte 52 contained in a vessel 50. Conductors 61 and 62 lead from the working electrodes 54a and 54b, respectively, to alternate switching terminals of a single-pole, two position switch 26 which is wired to one pole of a battery 20. The other pole of the battery is connected to the counter electrode, with an ammeter 22 in the conductor leading to the counter electrode 56. A voltmeter 24 is connected between the switch 26 and the reference electrode 58, completing the external circuit of the corrosion cell.

If the variant of the method applicable to the configuration of FIG. 4, a first potential is applied to working electrode 54a by appropriate action of the switch 26, and the resulting current measured by ammeter 22. A second potential is then applied to working electrode 54b and the resulting current measured. The two potentials are chosen in the Tafel region of the polarization curve and lie in the appropriate ranges, as described above with reference to the preferred variant of the method of the invention.

When plotting the results on the equivalent of FIG. 1, the results obtained by electrode 54a are used to determine point 'A' and the results obtained from electrode 54b are used to locate point 'B'. Extrapolation by graphical or mathematical methods to the intercept on the current density axis yields the desired value of the corrosion current.

Figure 5:
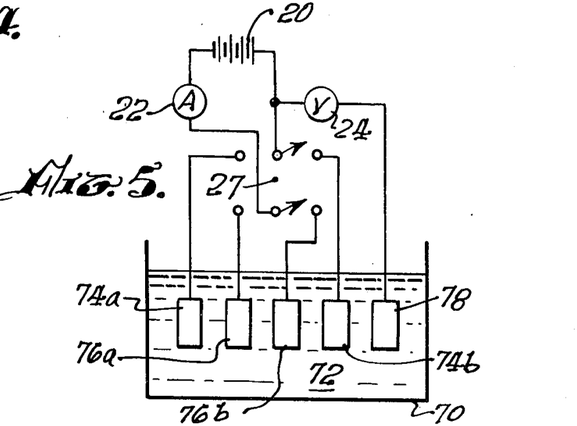
FIG. 5 is yet another schematic diagram of a corrosion current measurement cell with five electrodes.

The method of the invention may also be carried out using a corrosion cell with five electrodes, as illustrated in FIG. 5. A first working electrode 74a and a second working electrode 74b are so connected to alternate terminals of a two-pole, two-position switch 27 that moving the switch lever to either limit position will connect one or the other of the working electrodes to one terminal of a battery 20. Two counter electrodes 76a and 76b are also provided and are wired to the output terminals of the other pole of the switch 27, inter-connecting these electrodes, one at a time, to the other terminal of the source 20 with the interposition of ammeter 22.

A voltmeter 24 is also provided and measures the potential difference between the working electrode and a reference electrode 78.

In the determination of $I_{corr}$ the current is first applied across the corrosion cell formed by working electrode 74a and counter electrode 76a, the potential level — or current flow — being adjusted to represent a point in the region of the polarization diagram governed by the Tafel Law, with the potential exceeding 50 millivolts but not exceeding 200 millivolts, regardless of polarity. The switch 27 is then moved to its alternate position and working electrode 74b and counter electrode 76b placed into the circuit and the source 20 adjusted until the applied voltage read on voltmeter 24 is substantially above the first applied potential and lies in the range between 100 and 400 millivolts.

The material of the working electrodes 74 is, of course, the metallic composition whose corrosion rate in electrolyte 72, surrounding the five electrodes and contained within container 70, is to be determined. The counter electrodes 76 are identical to each other and may be formed from the same material as the working electrodes or of some other conducting composition.

The material of the reference electrode may be the same as that of the working or counter electrodes, or it may, by preference, be chosen from one of the previously described electrochemical reference electrodes known to the art.

One element of the apparatus required for the proper performance of the method of the invention has been omitted from the foregoing discussion of the several corrosion cell architectures with which the method is compatible; this relates to the use of a timing device to measure the elapsed time between the imposition of the forcing voltage and the recording of the resulting current. Such devices form no part of the invention as such and are well known in the chronometric arts. One particularly suitable form of the timer is an electrically driven unit which is automatically energized upon the closing of the circuit through battery 20 and which provides a signal — an alarm bell for example — at the conclusion of the present time period, usually of the order of a few tens of seconds.

The elapsed time is not chosen randomly but is the result of experimental insight into the transient state of a corrosion cell exposed to very high forcing potentials; prior to the development of steady-state reaction rates, the corrosion rate, and the cell current which is a function of the corrosion rate, passes through a number of distinct behavioral phases.

Figure 6:
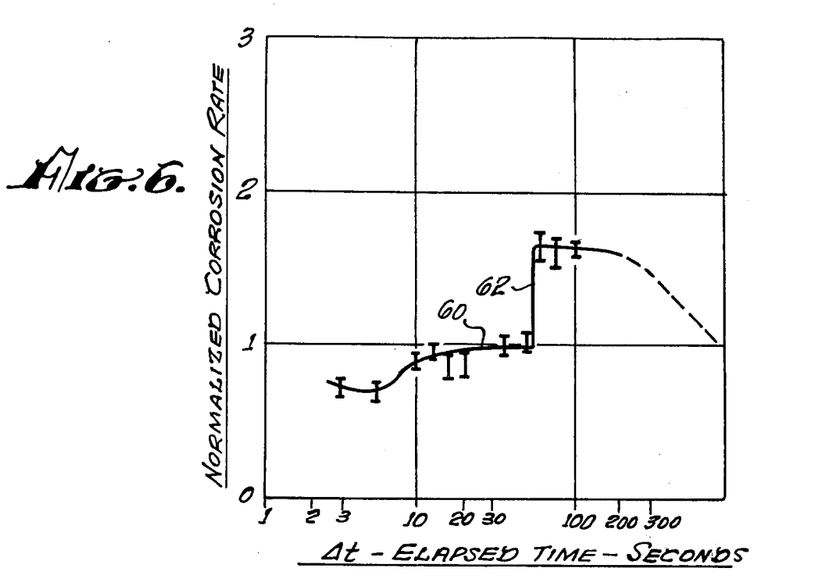
FIG. 6 is a graphical representation of the freely corroding corrosion current determined for a typical metal/electrolyte combination, as a function of the elapsed time between the imposition of the forced corrosion potential and the measurement of the resulting current.

The graph of FIG. 6 indicates such behavior, as measured in a corrosion cell wherein three electrodes are immersed in an electrolyte. All three electrodes in the cell whose behavior is shown in FIG. 6 were made from mild steel — AISI 1020 — and the electrolyte was a 3.5% solution of salt — Sodium Chloride — in water.

The abscissa of the plot indicates the time lag between applying the voltage and measuring the current, a logarithmic scale ensures clarity of illustration over the wide range of elapsed time periods. The ordinate records the measured corrosion rate, normalized with respect to the corrosion rate observable after the establishment of equilibrium conditions in the cell.

The plotted values correspond to the mean of several independent experimental measurements, the height of the bars represents the statistically significant range of results — plus or minus one sigma. It is readily observed that for elapsed time periods of less than ten seconds the results are unreliable; the shorter the time, the less likely it is to correspond to a measurement made for a slightly different time period. Between the 10 and 50 second elapsed time limits there is a substantially horizontal plateau — marked as segment 60 of the graph — which is at a level, within the expectable accuracy range, corresponding to the equilibrium corrosion rate. For elapsed time periods greater than 50 seconds the measured corrosion current jumps, as shown in line segment 62, suddenly to a much higher value than would be expected at equilibrium, until, as the time period is increased, the current decays to the value conventionally accepted as the steady-state corrosion rate.

It is the primary object of the invention to teach a method of corrosion rate measurement which takes advantage of the range of elapsed time periods of potential application in which the transient corrosion rate is the same, or very close to, the steady-state rate.

Clearly, the corrosion rate variation with time, as documented in FIG. 6, will vary with the nature of the working electrode, the nature of the electrolyte, the architecture of the cell and the potential levels applied to secure the current measurements. It is generally observed, however, that if the potential levels are chosen in accord with the teachings herein, typically at 100 and 200 millivolts, and the elapsed time held within the range of 10 to 50 seconds, the resulting measurement of freely corroding current, and the derived corrosion rate, will closely approximate the conventionally measured 'true' corrosion rate, and that the results can be obtained in a small fraction of the time and with the expenditue of little effort, as compared to the methods of the prior art.

The data included in Table I were derived from a closely controlled experiment in which four different metallic electrodes were subjected to the action of three different electrolytes and the resulting corrosion rates determined both by the method of the invention and by a prior art method. The method of the invention utilized three identical coupons as working, reference and counterelectrodes; the time delay between the application of the external forcing potential and the recording of the current flowing in the cell was ten seconds; and the applied potentials were 100 and 200 millivolts, respectively. The prior art reference method used a classical Tafel slope extrapolation — known as the E-log (I) method — in which the steady-state current and polarization values are plotted on semi-logarithmic paper and extrapolated back to the corrosion current intercept. The data were obtained on the same day, at room temperature, and with conditions as closely approximated for the two methods as possible. The two methods gave similar results.

TABLE I

| Electrode Material | Electrolyte | Corrosion Rate Prior Art Method | Determination Invention Method |
|---|---|---|---|
| Mild Steel | A | 330 mils/year | 350 mils/year |
| Mild Steel | B | 4.4 | 3.5 |
| Mild Steel | C | 15 | 10 |
| Copper | B | 0.01 | 0.01 |
| Zinc | A | 90 | 89 |
| Zinc | B | 33 | 34 |
| Zinc | C | 37 | 43 |
| Aluminum | A | 25 | 26 |
| Aluminum | B | 2.9 | 4.4 |
| Aluminum | C | 9.3 | 7.4 |

Electrolyte A had 3.5% NaCl dissolved in a 0.1N acquaeous solution of sulphuric acid; electrolyte B was a 3.5% NaCl solution in water; and electrolyte C was a mixture of 1 part water with 3 parts of methanol, saturated with NaCl.

The additional results presented in Table II cover a wide range of experimental conditions for the four representative metals of Table I, including two and three electrode measuring systems, different electrolytes, and the use of reference and counter electrodes with polarization characteristics differing from those of the working electrode. For each set of combinations the corrosion rate determined by the prior art E-log (I) method is also given, to provide a ready comparison with corrosion rates that would be considered accurate and reliable by those skilled in the art. The close correspondence between the results obtained by the method of the invention, for the several variants thereof employed, and those obtained by the reference method is obvious.

Test conditions were standardized for the experiments whose results are summarized in Table II: the imposed potentials were 100 and 200 millivolts; the time delays employed ranged between 10 and 20 seconds; and the measurements were performed at room temperature.

TABLE II

| WORKING ELECTRODE | ELECTROLYTE | E-log(I) METHOD | CORROSION RATES in MILS/YEAR METHOD OF THE INVENTION | | | |
|---|---|---|---|---|---|---|
| | | | THREE-ELECTRODE SYSTEM | | TWO-ELECTRODE SYSTEM | |
| | | | Identical electrodes | Different electrodes | Identical Electrodes | Different Electrodes |
| Mild steel | W | 0.027 | 0.032 | 0.034$^m$ | 0.024 | |
| | Y | 1.2 | 1.4 | 0.7$^p$ | 1.6 | |
| Copper | W | 0.073 | 0.073 | 0.091$^m$ | 0.04 | |
| | X | 54 | 64 | 43$^p$ | 41 | |
| | Y | 78 | 32 | 37$^p$ | 28 | |
| Zinc | W | 0.041 | 0.026 | | 0.037 | |
| | Z | 0.20 | 0.19 | 0.27$^q$ | 0.13 | 0.12$^s$ |
| Aluminum | W | 0.11 | 0.15 | 0.08$^m$ | 0.07 | |
| | Z | 0.061 | 0.061 | | 0.065 | 0.057$^r$ |

Figure 7:
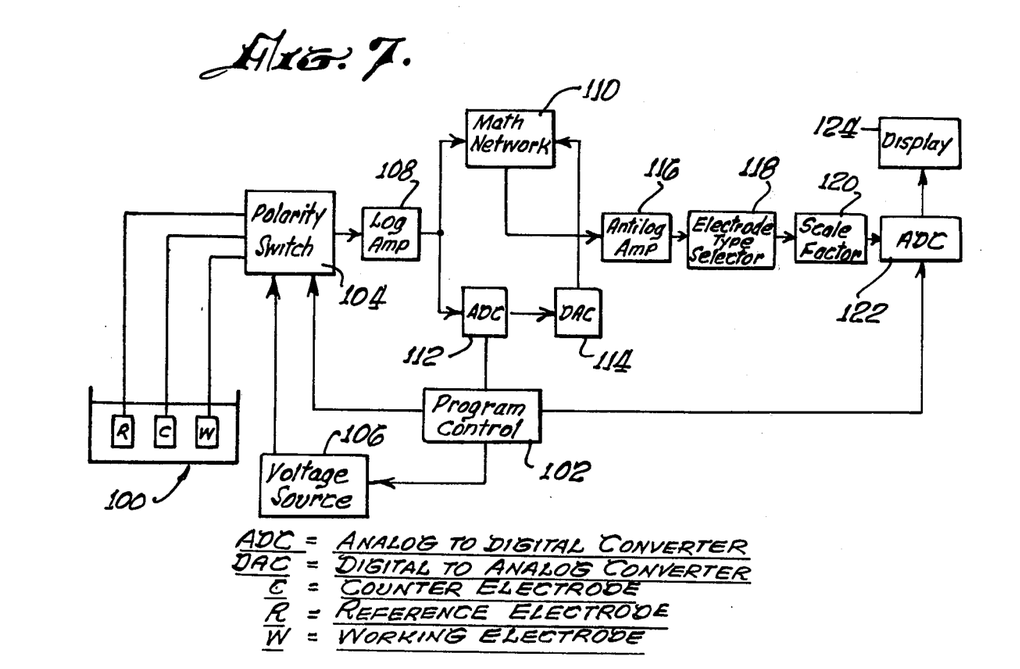
FIG. 7 is a schematic diagram of automatic instrumentation for the determination of the corrosion rate, according to the invention.

Electrolytes:
W - Glacial Acetic Acid
X - Acetic Acid, saturated with NaCl
Y - Concentrated (97.1%) Sulphuric Acid
Z - Absolute Ethyl Alcohol (100%)
Non-uniform Electrode systems:
$^m$CE=Platinum, RefE= Calomel
$^p$CE=Platinum, RefE = Silver Sulphide
$^q$CE=Platinum, RefE= Silver Chloride
$^r$Counter/Ref.Electrode= Silver
$^s$Counter/ref.Electrode= Silver Chloride The method and apparatus of the invention are readily adapted to automated instruments; a schematic diagram representing such an instrument is shown in FIG. 7; attached to a corrosion cell incorporating working, counter and reference electrodes, each of which is made from the material whose corrosion rate is to be determined in a given electrolyte.

The electrodes and electrolyte of the corrosion cell are encompassed in a measurement cell 100, generally corresponding to the embodiment of FIG. 2, as described above. The several electrodes are connected to a polarity switch 104, which incorporates switching means permitting the reversal of potentials switching across the counter and working electrodes, as well as current measurement means. The functioning of the polarity switch is governed, along with the rest of the instrument, by a program control 102, which commands a specific sequence of steps governing the instrument as a whole, provides a time reference — derived from the 60 Hertz supply current — and a high-frequency clock — derived from an astable multivibrator at about 100 kHz — for the signal converters.

A voltage source 106 supplies the required potentials to the polarity switch, generally at 100 and 200 millivolts, under the control of the program control module 102.

The current in the corrosion cell 100 is continuously monitored by the ammeter integral with the polarity switch 104 and a signal proportional to the current is passed onto a logarithmic amplifier 108. The amplifier 108 produces a signal proportional to the logarithm of the current level, and this signal is made available both to a computing network 110 and to an analog-to-digital converter 112 followed by a digital-to-analog converter 114.

The combination of the computing module 110 and of the signal converting module 112/114 produces, under the command of program control 102, a summed potential which is proportional to the logarithm of the freely corroding cell current. The equation solved is $$\ln i = 2 \ln i_1 - \ln i_2$$

where $i_1$ represents the current flowing at an impressed potential equal to $e_1$ and $i_2$ represents the current flowing at an impressed potential equal to twice $e_1$. It should be noted that the computing scheme is independent of the actual value of the impressed potential, so that minor changes in the desirable voltage levels may be simply accomplished by altering the voltage source 106, as long as the two potentials used to obtain the two points required to define the exponential slope in the Tafel region are in a two-to-one proportion to each other. As already mentioned, the levels of 100 and 200 millivolts have been found to satisfy the requirements for a large variety of corrosion cells and these values may be incorporated into the voltage source 106 of a standard instrument.

Since the output signal is proportional to a logarithm, it is passed through an antilog network 116 to convert the output to an absolute value of the current.

An electrode type selector 118 and a scale factor selector 120 are also in the signal path; the function of the former is to allow geometrical and other constraints relating to the material of the electrodes and their arrangement to be factored into the output, while the latter allows the display to be more efficiently utilized with respect to signals of widely varying amplitude.

The operating sequence of the instrument of FIG. 7 is as follows: The program control switches on the voltage source 106 at the first potential level — chosen in the range between 50 and 200 millivolts — and applies this potential across the working and counter electrodes in the cell 100; this potential level is maintained for a period designated as $\Delta t$ — selected in the range between 10 seconds and 50 seconds — at the end of which the computing network is signaled to record the current level for computation, and the voltage source is switched to a potential twice as high as the first — chosen in the range between 100 and 400 millivolts; this new potential level is maintained for a duration equal to $\Delta t$, and the computing network again signaled to record the current level at that time; the display is next authorized to accept the newly computed value of the freely corroding current and to display it. The display 124 is so controlled that the last output value authorized by the program control remains lighted thereon until replaced by a new set of data. The program control next reverses the role of the working and counter electrodes, by suitable messages to the polarity switch 104, and applies two potential levels of the opposing polarity and increasing magnitude, at precisely the same voltage values and for the same periods of time as described above. This procedure depolarizes the electrodes and could, if so desired result in an output signal corresponding to the intercept of the Tafel curve representing the opposing polarity.

For a number of reasons it is deemed unnecessary to follow this procedure and the instrument is generally programmed to compute outputs for the cathodic branch of the corrosion characteristic only; applying anodic potentials only to depolarize the corrosion cell 100.

Whenever a new sample of electrolyte, or a new set of electrodes is introduced into the corrosion cell 100, there is a possibility that some external contaminant may affect the result of the measurement. For this reason the preferred embodiment of the instrument of the invention is so programmed that it will cycle through the aforementioned steps continuously until stopped by the operator. This produces a new output display at time intervals corresponding to four times the selected period $\Delta t$ — that is, every two minutes, approximately — and the user can monitor the achievement of consistent successive readings, indicating that external influences are not affecting the output.

The circuit of the instrument described is highly schematic, and is illustrative only in a general way of the manner in which the method of the invention may be mechanized to produce corrosion rate data rapidly and economically. Additional components, such as means for continuously stirring, aereating, or varying the temperature of the cell 100 may be provided, and the latter may be interconnected with the program control and display modules to track the corrision rate as function of the system temperature, for example.

It should also be noted that all variants of corrosion cell architecture described hereinabove may be connected to instruments of this general type, with some modification of program control function, if necessary.

A person skilled in the art of instantaneous corrosion rate determination may, upon exposure to the teachings herein, find certain changes that will be congenial in the described experimental apparatus, in the method of supplying and controlling the external forcing circuit, or in the manner of applying and using the required instrumentation. Such changes, not affecting the substance of the method, shall be deemed within the scope of the invention, which is limited only by the appended claims.

The inventors claim:

1. A method for determining the freely corroding current density of a metallic substance immersed in an electrolyte, comprising the steps of:
   providing a working electrode formed of said substance,
   providing a counter electrode formed of a conductive material,
   providing a reference electrode formed of a conductive substance,
   immersing said three electrodes in said electrolyte,
   establishing by external means a first potential difference, not less than 50 millivolts in magnitude, across said working and reference electrodes,
   measuring the current flow induced by said first potential difference through said counter electrode after the elapse of a predetermined first time period, said first time period being substantially shorter than the time required to establish equilibrium current flow upon the imposition of said first potential difference,
   measuring said first potential between said working and reference electrodes,
   recording said current and said potential difference,
   establishing by said external means a second potential difference, substantially higher in magnitude than said first potential difference, between said working and reference electrodes,
   recording said second potential difference and the current resulting therefrom after the elapse of a second pre-determined time period, said second time period being substantially shorter than the time required to establish equilibrium current flow upon the imposition of said second potential difference,
   converting said current measurements into current density measurements,
   deriving the linear equation passing through the pair of coordinate points represented by the measured first and second potential differences and by the logarithms of the corresponding measured current densities, and
   determining, by means of said equation, the freely corroding current density at zero applied potential difference.

2. The method of claim 1 wherein said first potential difference is selected in the range between 50 and 200 millivolts and said second potential difference is selected in the range between 100 and 400 millivolts.

3. The method of claim 2, wherein said conductive substance is said metallic substance.

4. The method of claim 1 wherein said conductive material of the counter electrode is said metallic substance.

5. The method of claim 4, wherein, additionally, said conductive substance is also said metallic substance.

6. The method of claim 1, wherein said pre-determined time periods are between ten seconds and fifty seconds.

7. The method of claim 1, wherein said conductive substance is selected from the following materials:
   platinum,
   calomel,
   copper/copper sulphate, and
   silver/silver chloride.

8. The method of claim 1, wherein said linear equation is solved by plotting said pair of coordinate points on graph paper and extending a straight line there through to its intercept on the logarithmic current density axis.

9. A method for determining the freely corroding current density of a metallic substance immersed in an electrolyte, comprising the steps of:
   providing a first working electrode formed of said substance,
   providing a second working electrode formed of said metallic substance,
   providing a counter electrode formed of a conductive material,
   providing a reference electrode formed of a conductive substance,
   immersing said four electrodes in said electrolyte,
   establishing by external means a first potential difference, selected in the range between 50 and 200 millivolts, across said first working and said reference electrodes, measuring the current flow induced by said first potential difference through said counter electrode after the elapse of a predetermined first time period, said first time period being substantially shorter than the time required to establish equilibrium current flow upon the imposition of said first potential difference, measuring said first potential difference between said first working and said reference electrodes, recording said first potential difference and said current induced thereby, establishing by said external means a second potential difference, substantially higher in magnitude than said first potential difference and selected in the range between 100 and 400 millivolts, across said second working and said reference electrodes, measuring and recording said second potential difference and the current flow resulting therefrom through said counter electrode after the elapse of a second pre-determined time period, said second time period being substantially shorter than the time required to establish equilibrium current flow upon the imposition of said second potential difference, converting said current measurements into current density measurements, deriving the linear equation passing through the pair of coordinate points represented by the measured first and second potential differences and by the logarithms of the corresponding measured current densities, and determining, by means of said equation, the freely corroding current density at zero applied potential difference.

10. The method of claim 9, wherein said conductive substance is selected from the following materials:
platinum,
calomel,
copper/copper sulphate, and
silver/silver chloride.

11. The method of claim 9 wherein said conductive material of the counter electrode is said metallic substance.

12. The method of claim 9, including the additional steps of:
providing a second counter electrode of a conductive material,
immersing said second counter electrode in said electrolyte,
establishing said second potential difference across said second working and said reference electrodes, and
measuring and recording said second potential difference and the current flow resulting therefrom through said second counter electrode after the elapse of said second predetermined time period.

13. The method of claim 12 wherein said conductive material of said first and second counter electrodes is the same as said metallic substance of said first and second working electrodes.

14. The method of claim 9, wherein said predetermined time periods are intermediate between ten seconds and fifty seconds in duration.

15. A method for determining the freely corroding current density of a metallic substance immersed in an electrolyte, comprising the steps of:
providing a working electrode formed of said substance,
providing a counter electrode formed of a conductive material,
immersing said two electrodes in said electrolyte,
establishing by external means a first potential difference, not less than 50 millivolts in magnitude, across said working and counter electrodes,
measuring the current flow induced by said first potential difference through said working electrode after the elapse of a predetermined first time period, said first time period being substantially shorter than the time required to establish equilibrium current flow upon the imposition of said first potential difference,
measuring said first potential difference between said working and said counter electrodes,
recording said first potential difference and said current induced thereby,
establishing by said external means a second potential difference, substantially higher in magnitude than said first potential difference, between said working and said counter electrodes,
recording said second potential difference, and the current flow through said working electrode induced thereby after the elapse of a second pre-determined time period, said second time period being substantially shorter than the time required to establish equilibrium current flow upon the imposition of said second potential difference,
converting said current measurements into current density measurements,
deriving the linear equation passing through the pair of coordinate points represented by said measured first and second potential difference and by the logarithms of the corresponding measured current densities, and
determining, by means of said equation, the freely corroding current density at zero applied potential difference.

16. The method of claim 15 wherein said first potential difference is selected in the range between 50 and 200 millivolts and said second potential difference is selected in the range between 100 and 400 millivolts.

17. The method of claim 16 wherein said conductive material of the counter electrode is said metallic substance.

18. The method of claim 15, wherein said conductive material is selected from the following group:
platinum,
calomel,
copper/copper sulphate, and
silver/silver chloride.

19. The method of claim 15 wherein said linear equation is solved by plotting said pair of coordinate points on graph paper and extending a straight line therethrough to its intercept of the logarithmic current density axis.

20. The method of claim 15, wherein said predetermined time periods are selected in the range between 10 and 50 seconds.

* * * * *